(12) United States Patent
Kanevsky

(10) Patent No.: US 6,934,581 B2
(45) Date of Patent: Aug. 23, 2005

(54) NON-INVASIVE METHOD FOR DISEASE DIAGNOSIS

(75) Inventor: Alexander Kanevsky, Arad (IL)

(73) Assignee: Medex Screen Ltd., Arad (IL)

(*) Notice: Subject to any disclaimer, the term of this patent is extended or adjusted under 35 U.S.C. 154(b) by 413 days.

(21) Appl. No.: 10/210,223

(22) Filed: Aug. 1, 2002

(65) Prior Publication Data
US 2003/0045809 A1 Mar. 6, 2003

(51) Int. Cl.$^7$ ................................................ A61B 5/05
(52) U.S. Cl. ...................................................... 600/547
(58) Field of Search ................................ 600/547, 548, 600/384, 372; 128/897, 898

(56) References Cited

U.S. PATENT DOCUMENTS 3,971,366 A * 7/1976 Motoyama .................. 600/384
4,557,271 A * 12/1985 Stoller et al. ............... 600/547

* cited by examiner

Primary Examiner—Max F. Hindenburg
Assistant Examiner—Brian Szmal
(74) Attorney, Agent, or Firm—Hodgson Russ LLP

(57) ABSTRACT

A diagnostic method comprises selecting 24 biologically active points (BAPs), measuring the skin resistance at the points, plotting the average resistance for the points as an isoelectric line and defining a normal corridor. A stimulation is applied to each of the points and thereafter the skin resistance is once again measured. The results of the two sets of measurements are compared and diagnostic conclusions are reached from their comparison.

11 Claims, 5 Drawing Sheets

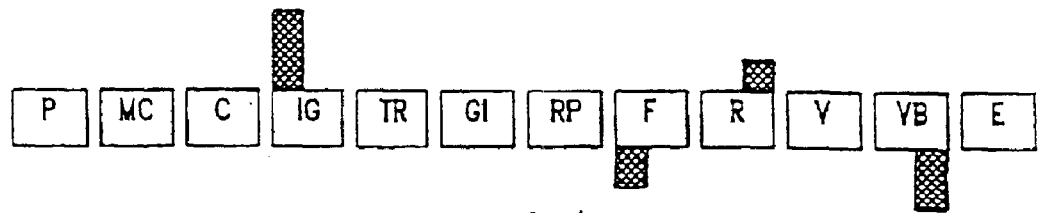
Graph 1
(Graph of the first examination)
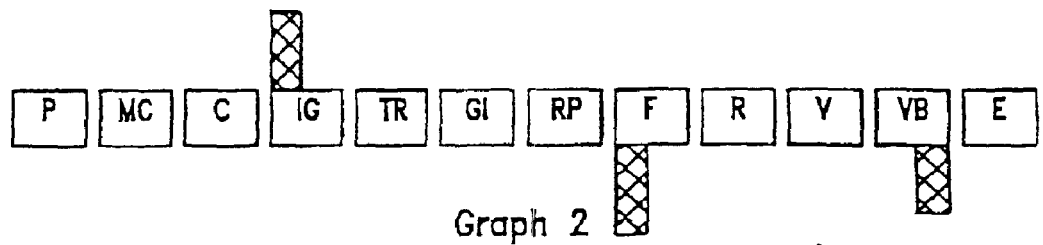
Graph 2
(Graph of the second examination)
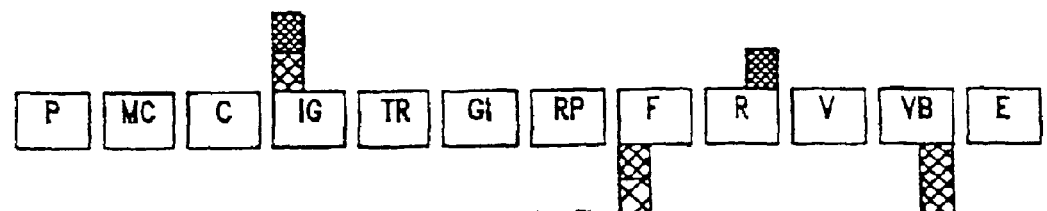
Graph 3
(Superposition of the graphs)

NON-INVASIVE METHOD FOR DISEASE DIAGNOSIS

This application is being filed as a national phase II entry in the U.S.A. of international patent application Ser. No. PCT/IL01/00086, (filed Jan. 29, 2001) which claims priority to Israel patent application Ser. No. 134381 (filed Feb. 3, 2000).

FIELD OF THE INVENTION

This invention relates to a method for the non-invasive diagnosis of actual diseases and of potential disease activity.

BACKGROUND OF THE INVENTION

It has been known for some time that there are points in the human body in which the electric conductivity of the skin is higher than in the surrounding area, as a result of some actual or potential pathological phenomena. It has also been found that these points correspond each to a particular part of the body. All the points corresponding to the same part are arranged in lines that have been called "meridians". Thus, a lung meridian appears in lung disease, a stomach meridian in stomach disease, and so on. These facts are discussed, e.g. in U.S. Pat. No. 5,339,827. Further, they form the object of publications of the Japanese Society of Ryodoraku Medicine (JSRM), the Japan Acupuncture Moxibustion and Ryodoraku Medical Society (JAMR), and others. Explanations for the above phenomena have been offered, but this invention is independent of such explanations and is only based on the existence of the phenomenon.

The points of the body in which the electrical resistance is measured on the skin have been called BAPs (biologically active points). It has been found that for each meridian, there is one BAP that is representative of that meridian, and which provides an average value for said meridian. A list of the BAPs, with the symbols by which they will be referred to hereafter and their locations is shown in FIG. 1. Explanation with respect to each BAP symbol is given in the following table:

| BAP | EXPLANATION |
| --- | --- |
| P9 | The origin point of Lung Meridian Located on the wrist joint (the side of the palm) in the hollow near the thumb. |
| MC7 | The origin point of Heart Governor Meridian. Located in the middle of the wrist joint (the side of the palm). |
| C7 | The origin point of Heart Meridian. Located on the wrist joint (the side of the palm) in the hollow of the fifth finger. |
| IG4 | The origin point of Small Intestine Meridian. Located on the side of the hand, near the fifth finger in the hollow near the wrist. |
| TR4 | Triple Heater Meridian origin point Located in the middle of the wrist joint (back of the hand) between the third and the fourth finger tendons. |
| GI5 | Large Intestine Meridian origin point. Located on the border of the hollow (the one separating the thumb and the index finger) and the side of the wrist. |
| RP3 | Spleen-Pancreas Meridian origin point. Located on the inner side of the foot in the hollow behind the first toe's mound. |
| F3 | Liver Meridian origin point. Located on the upper side of the foot, in the narrowest part between the first and second toe's tendons. |
| R3 | Kidney Meridian origin point. Located in the middle between the inner part of the ankle-bone and the achilles tendon. |
| V65 | Bladder Meridian origin point. Located on the outer side of the foot, in the hollow behind the fifth's toe's mound. |
| VB40 | Gall Bladder Meridian origin point. Located near the front lower part of the ankle-bone. |
| E42 | Stomach Meridian origin point. Located on the highest point of the upper part of the foot, between the second and third toe's tendons, where a dorsabis pedis is. |

In addition to these average points, there is also an announcement point for each meridian that is representative of a particular organ, or organ system. The announcement points are points on the body surface which develop sensitivity and/or soreness when the corresponding organs are affected and in which generally occur skin temperature changes. In conventional medicine zones, called Zakharin-Ged reflected sensitivity zones, are known and widely used in diagnostics. The announcement points generally coincide with the reflected sensitivity zones.

Similarly, there are other points, known as sympathetic points, which are representative of the stimulation state of particular segments of the sympathetic nervous system. If the ratio of the electroskin reistance of an announcement point to that of the corresponding sympathetic-point (expressed in kΩm) is less than 0.75, it may signal an acute process in an organ within the segment being examined. If the ratio is higher than 1.25, a chronic affection may be present in a representative organ. If kΩm are converted into current intensity exponents A, the ratio will change in the following way: If the ratio of the intensity of current of an announcement point to the intensity of current of the corresponding sympathetic-point exceeds 1.25, the process in the representative organ is acute, and vice versa.

Finally, there are also "energy reference point". These are points in which electrical resistance of the skin is very stable and only changes in cases of serious disease. In principle, there are six such points, which have been designated by the symbols T1, T14, T28, J1, J18, J24 (see Macheret, E. L., "Reference of the Reflexotherapy", Moskva, 1982; Voll, R., "Topographische Lage der Messpunkte der Elektroakupunktur", Uelsen, 1976; and Niboyet, E., "Traite d' Acupuncture", Paris 1974).

The ratio of the skin resistance in a tested point, related to an organ, to the skin resistance in one of the energy reference points indicates whether the organ is healthy or affected. Generally, that ratio should be from 0.75 to 1.25 for a healthy organ and is outside that range for an affected one. As a reference point, it is generally preferred to choose J18 for comparison with tested points in the front surface of the body and T14 for comparison with tested points in the rear surface of the body.

In one diagnostic method, the electrical resistance of 12 BAPs on each side of the body (i.e., 24 points total) is measured. The average resistance for all of these 24 points is then plotted as a horizontal line, referred to as the "isoelectric" line. Using similar data obtained from a group of healthy individuals, an upper and lower limit is plotted above and below each isoelectric line, thus defining a "normal corridor". The isoelectric line and the normal corridor thus constitute an average diagram, upon which individual data may be inserted and compared.

In order to diagnose the situation of an individual, the electrical resistance of the skin at each of the 24 BAPs is measured and converted into electric current intensity by applying Ohm's law. Then, if the resulting intensity values cross the upper borderline of the diagram which represents the said normal corridor, this indicates that an acute process is going on in the organ. If the resulting intensity values cross the lower borderline of the diagram which represents the said normal corridor, this indicates that a chronic process is present.

Results obtained by this method may then be used to direct the acupuncturist or other practitioner in planning the appropriate treatment. The way of tracing an isoelectric line and a normal corridor is described in the following publications: Nakatani, Y., Yamashyta, K., "Ryodoraku Acupuncture". Tokyo, 1977; and Hyodo, M., "Ryodoraku Treatment, Osaka, 1975".

A major problem associated with the diagnostic method described above is that the electrical resistance values obtained may be influenced by many factors unrelated to the presence of a pathologic condition, for example, cigarette smoke inhalation, consumption of beverages containing alcohol or caffeine, exercise, and so on. Such factors may therefore lead to false diagnostic conclusions.

It is an object of the present invention to provide a diagnostic method, based on the measurement of electrical resistance at the skin surface at BAPs, that overcomes the problem of misleading or unreliable results due to factors unrelated to pathological processes.

Other objects and advantages of the invention will appear as the description proceeds.

SUMMARY OF THE INVENTION

The method according to the invention comprises selecting 24 BAPs, measuring the skin resistance at said points, plotting the average resistance for said points as an isoelectric line and defining a normal corridor, as in the prior art, and is characterized in that stimulation, preferably electrical as hereinafter more fully described, is applied to each of the said points and the skin resistance is measured once again at said points after applying the stimulation. The points' stimulation may be performed by two methods: mechanical and electrical. When using the mechanical method E 36 and GI 4 points are massaged. However, the physician carrying out the examination may find it difficult to precisely measure out the strength with which the points should be affected (pressed), which may cause inaccuracies in the stimulation. Thus, electrostimulation, being precisely measured for all the four points, is preferable.

Further, according to the invention, the results of the two sets of measurements are compared, e.g. by superimposing them on a computer display screen, and diagnostic conclusions are reached from their comparison. If a result obtained from the first set of measurements falls outside the normal corridor, this is considered a potential indicator of disease activity. If the corresponding result obtained from the second set of measurements (after stimulation) also lies outside the normal corridor, this is considered as a true indication of the presence of a disease. If, however, the corresponding result from the second set of measurements falls within the normal corridor, then the first measurement is considered not to be an indication of a true disease state and is therefore disregarded.

An illustrative example of the superposition and comparison of the two sets of measurements is given in FIG. 2. Let us assume that after the first measurement, the average exponent (based on which the isoelectric line is designed) equals 5 microamperes. Then the normative corridor's (the span of which is 2.5 microamperes, 1.25 above and below the isoelectric line) upper border will be situated on the mark of 6.25 microamperes, while its lower border will reach 3.75 microampere level. Let us assume that after the second measurement (following the underload probes), the average exponent for these tests equals 6 microamperes. Then the upper border of the normative corridor for the second series of measurement will be on the mark of 7.25 microamperes, while the lower one will be on the level of 4.75 microamperes. The isoelectric lines and the normative corridors are combined (superimposed) using appropriate software, which allows for easy viewing and interpretation of the graphs.

The stimulation, carried out according to the invention, may be called "electropunctural stimulation". It is also referred to as "underload probing". The term "load probing" is a standard term for medical manipulations, whose aim is to make some or other of the organism's systems, in our case, the system of homeostasis, more active. Homeostasis is the system which regulates the production and the action (influence) on the target organs of hormones, enzymes, amines; the system of regulating the blood circulation; the immune system's functioning, nerve-muscle connections, metabolic processes. The doctrine of homeostasis is at the basis of conventional ideas about man's normal and pathological physiology; it constitutes its main section. In fact, homeostasis is the state of all the processes of the organism being balanced; when homeostasis is disturbed, it means a disease has set in. The system of homeostasis reacts to a certain extent to all the external and internal influences, like changes in the weather, acclimatizing, physical or psychological stress, alcohol consumption, food consumption, intake of medicine, physiotherapy, any organ's pathology, etc. Under the influence of electropunctural stimulation, defensive response reactions of the homeostasis system become active.

The underload probing is conducted with the help of a "throughskin electroneirostimulator" device. Such devices produced everywhere in the world, and is widely used by acupuncture practicioners for stimulating BAPs for various purposes (for example, when stimulating the points in the peripheric nerves'projection, their pain sensibility is suppressed as segmental input on the spinal cord level is blocked). They are pproduced e.g. by Pantheon Research® under the name Electro-S timulator 4-C and by Solar Wide Industrial Ltd. of Hong Kong under the name Search N' Stim ™. They are devices that generate a pulsed current and permit to apply it to the skin The output voltage of the device is 9–12 V and it produces pulsed electric current with short rectangular pulses (with a frequency of about 100 Hz). The intensity of the stimulation is regulated by changing the intensity of the current (between 0 and 500 $\mu$A) till the expected sensation—i.e., the feeling of tingling under the electrode—appears. This serves as a starting point for the stimulation session time countdown. The tingling sensation threshold for a patient is the same at each of the treated points, and appears on an average when the current reaches about 100 mkA.

Details of how the stimulation is preferably effected will be given hereinafter.

BRIEF DESCRIPTION OF THE DRAWINGS

In the drawings:

FIG. 2 schematically illustrates the comparison of two sets of skin resistance measurements made according to an embodiment of the invention;

DETAILED DESCRIPTION OF THE PREFERRED EMBODIMENTS

The method of the invention, according to a preferred embodiment, is carried out by the following steps.

1. Measuring the electric resistance of the skin at the 24 BAPs in the feet and hands of the patient (all measurements being held within the 0–20 micro-Amperes range of current);

2. Applying a stimulation to the BAPs by means of an electropunctural stimulator;

3. Repeating the measurement of the electric resistance of the skin at the 24 BAPs;

4. Taking electric resistance measurements of the 10 announcement points on the abdomen;

5. Measuring the electrical resistance of the skin at the 12 sympathetic points in the paravertebral zone (bladder meridian);

6. Measuring the reference skin resistance at announcement points (the middle anterior meridian) and at sympathetic points (the middle posterior meridian), the number and location of which depend on the organ being diagnosed;

7. Mathematically processing the collected information by a predetermined correlative algorithm.

8. Showing the resulting conclusion on display and/or printing it out graphically and/or in figures.

The above numbers of announcement points and sympathetic points are measured when diagnosing GIT diseases. In other cases, smaller numbers may be measured, but in general the number of announcement points and sympathetic points to be measured depends on the system to be diagnosed.

The stimulation is preferably carried out as follows: GI4 on the left arm, GI4 on the right arm, E36 on the left leg (calf) and E36 on the right leg (calf) are stimulated each for one minute. It is possible to stimulate two points simultaneously, firstly on the arm and then on the leg, or even all four points simultaneously, if the stimulator is so structured as to permit it. GI4 and E36 are called "general influence points", because their stimulation makes all the systems in the organism more active simultaneously (see Zang, X., "Acupuncture, Electrotherapy", 1990; Lee, M., "Cardiovascular effects of acupuncture at Tsu San Li", 1975; Kaada, B., "Mechanisms of acupuncture analgesia", 1974; and Portnov, F., "Electropuncture", 1980).

The collected information is processed according to the following steps.

Figure 1:
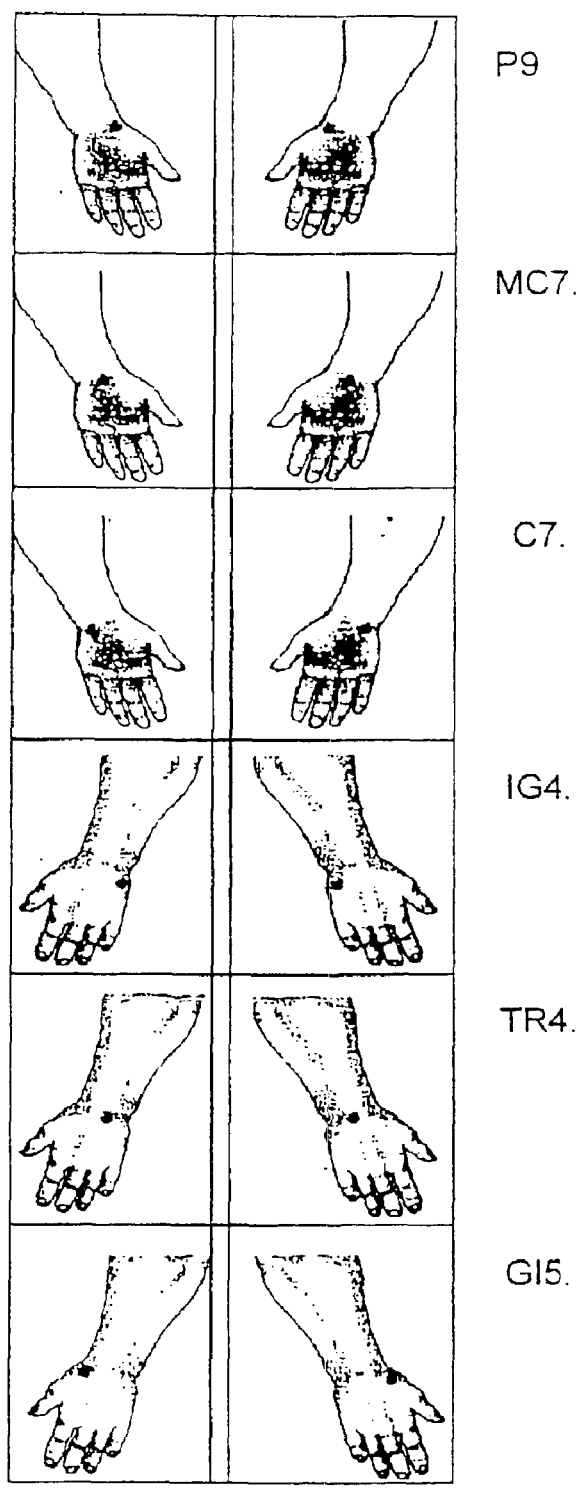
FIG. 1 shows a list of the BAPs.
Figure 1:
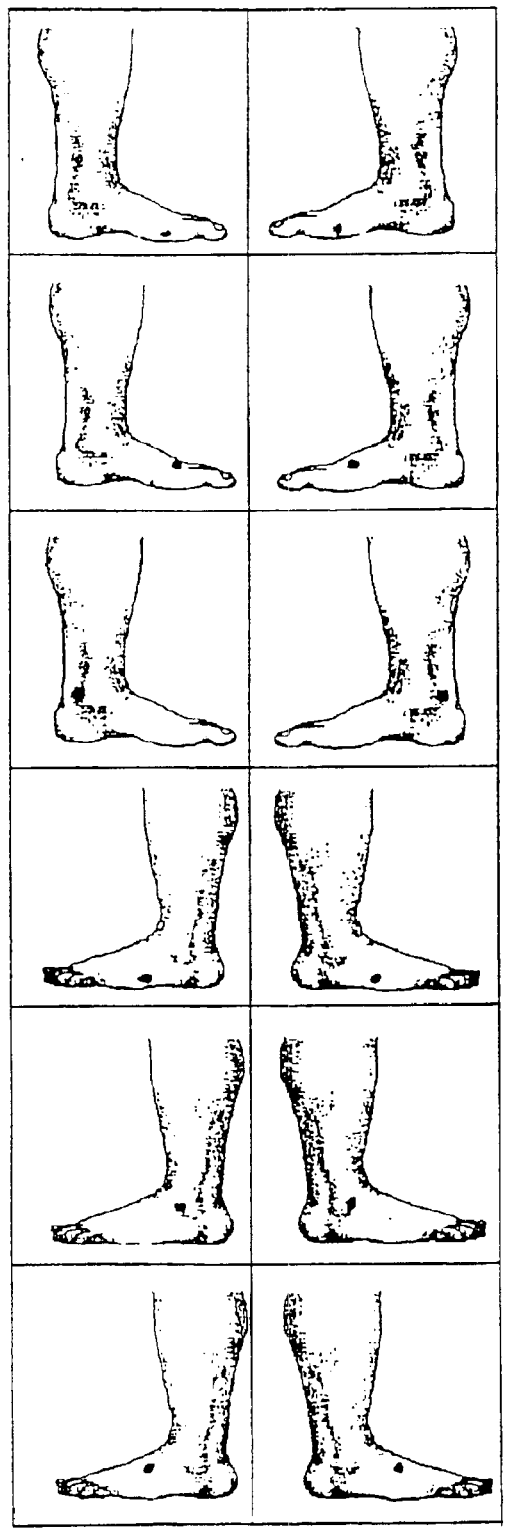
Figure 3:
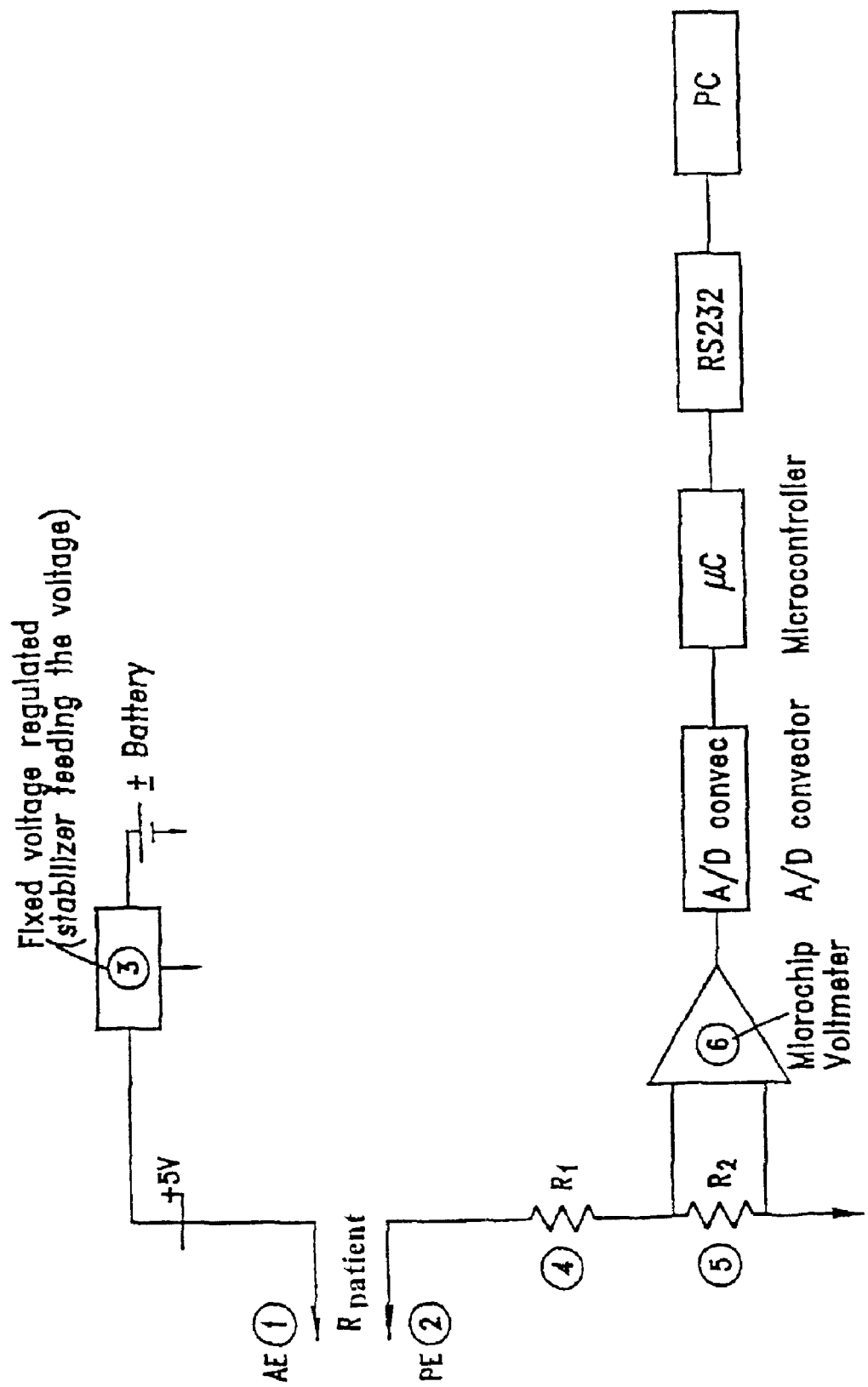
FIG. 3 is a block diagram schematically illustrating an apparatus and a process for the measurement of the skin resistance according to an embodiment of the invention.

1. The value of the electroskin resistance is measured and is expressed in k$\Omega$. The higher the electroskin resistance value, the lower the value of the current power in mkA and vice versa. The manner of this measurement is illustrated in the scheme of FIG. 3. The active electrode (1) touches the patient's arm. The passive electrode (2) is attached to his/her wrist. When the device is turned on, an electric chain is created. A stabilizer feeding the voltage (3) of 5 Volts is introduced into the scheme. Also, two resistors—R1 (4) and R2 (5) are included, with a summary resistance of 250 k$\Omega$. The intensity of current in the chain without a patient does not exceed 20 microamperes (according to Ohm's law: I=U (R1+R2), where U=5 V; R=250 k$\Omega$Q I=20 microamperes). When a patient is included in the chain, he/she naturally brings his/her resistance into the chain. Then, the intensity of the current is calculated, according to the following formula:

I patient=U/(R1+R2+R patient), where U=5 V; R1=230 k$\Omega$; R patient and I patient are unknown.

The formula may be expressed differently: U=(I patient×R1)+(I patient×R2)+(I patient×R patient).

The intensity of current in the chain is constant throughout the testing. The voltage of 5 V is the summary voltage along the R1 resistor section, the patient's R patient section and the R2 resistor section. Within the R2 resistor section, a voltmeter scheme (6) is placed, which measures the voltage decrease along the resistor section with the resistance of 20 k$\Omega$. Thus, the intensity of current within the chain (going through the BAP) can be calculated, using the following formula:

I patient=U microchip/R2, where R2=20 k$\Omega$; U=the exponent measured by the microscheme.

The data of the intensity of current within the chain (i.e., the values of the current passing through the BAP), are transmitted to an A/D convector, where they are converted into bytes, transmitted to the computer by the microcontroller through the RS-232 port.

Knowing the intensity of current within the BAP chain, it is easy to calculate its electrical skin resistance, having introduced the value of the current intensity into the following formula:

I patient=U/(R1+R2+R patient), R patient=U/I−(R1+R2).

The only unknown value here is the patient's resistance (which is the electroskin resistance of the BAP).

It has been proven that in the announcement points, electric current readings in mkA increase (i.e., their electroskin resistance decreases) following active processes, while in segmental points the same thing happens following lengthy, inert processes.

2. The readings from symmetrical points are compared. There exist 12 symmetrical (twin) meridians and two middle (non-twin) ones. All the twin meridians have a left and a right branch. That is why all the listed meridian points are twin points: they are localized both on the left and on the right branches of these meridians. Symmetrical points are those found on the same meridian, but on its different branches, both their localization and their number being identical, for example, P9 on the left and P9 on the right (on both hands); E 25 on the left and E 25 on the right (on the abdomen). If the difference in the readings of the symmetrical points on the front surface of the body exceeds 25%, it signals that there is an active process (acute or chronic one in an acute condition) in the given index zone. If there is a difference of less than 25% on the back, it is a sign of an inert process going on in the corresponding organ.

3. The readings of corresponding announcement points and segmental points (correlated along the segmental chain) are compared. If the difference between the data of the announcement points and the corresponding segmental points exceeds 1.25, it signals an active process going on in the organ situated in the examined segment, while if the ratio is less than 0.75, it indicates a sub-acute process therein.

4. The index of each announcement point is compared with that of the reference point, viz. relatively permanent electroskin resistance point J18. If the ratio exceeds 0.75–1.25, it means there is a problem in the organ this announcement point is responsible for; if the ratio is higher than 1.25, it may signal an active process. If it is less than 0.75, it is an indication of a tendency towards an inert, sub-acute process.

5. Each segmental point's readings are compared to the index of a "relatively permanent electroskin resistance" T14-point. If the ratio is higher than 1.25, it may signal an inert, sub-acute process in the corresponding organ; if it is less than 0.75, an acute process is suspected.

6. The resulting coefficients, viz. the numerical data obtained from all the foregoing operations, are analyzed and compared with each other and, based on the results obtained, an opinion on the condition of a given organ and the processes going on there is formed.

It is to be noted that it is important to take into account the ratios determined by steps 4 and 5. There may be, for example, a situation when an active (acute) process is going on simultaneously in symmetrical organs (as in both the ascending and descending sections of the large intestine), or it may be that only one announcement point corresponds to a given organ (as in the case of the stomach). In such situations, the reading comparisons of step 2 are inadequate, while the ratios determined in step 4 may indicate an acute process going on in the corresponding organ.

Before testing, the BAPs must be treated with 70% ethyl alcohol solution to avoid possible effects of sebum, humidity or impurities that may be present on the skin, on the results of the test. Since the points are affected by very low (0–20) electric current, no damage is done to their energy potential during the very short time of testing. They can be scanned up to five times each. This allows use of special underload tests. These tests are conducted with the help of the electropunctural device (electroneurostimulator) hereinbefore discussed. It acts upon special BAPs on the extremities (4 points) for one minute. It is with the help of these underload tests that one can differentiate between functional and organic disorders of the digestive organs. The effect for this underload test lasts for about 10 minutes. During this time, the physician can repeat the measurements on the 24 source points on the extremities and on the 22 points (announcement and sympathetic) on the patient's body. The information collected from the 48 source points (both before and after the underload test) is analyzed separately from the data received from announcement points and sympathetic points.

The data received from the 24 BAPs are added together and divided by 24. The resulting averages are used to draw a diagram in which they are plotted as the ordinate on the vertical axis, in which the BAPs are marked as the abscissa, and afterwards are connected by a line into a curve, the so-called individual isoelectrical curve of the given patient. Above and below this isoelectrical curve are another 2 parallel lines denoting the normative corridor of the patient. The width of the corridor depends on his/her energy potential.

The notion "human energy potential" is a composite notion. The man's energy potential consists of physiological processes in the organism, such as the interrelation between the functioning of the cortical and subcortical structures of the central nervous system; the hormonal balance of the organism; the immune system's condition; its blood circulation and lymph flow; the way its inner organs function and much more. A given person's energy potential is determined by the condition of his/her homeostasis. The energy potential manifests itself through the physical parameters of the BAPs, representative of organs and systems. Measuring their electroskin resistance, one can evaluate the given organism's energy potential. The width (span) of the normative corridor taken from literature is 2.5 microamperes with fluctuations of 25%, depending on the average value of the given patient's electroskin resistance.

The 24 BAPs examination normal corridor span (range) has been calculated by many authors (J. Nakatani, 1956; M. Hyodo, 1977; V. Portnov, 1982) and is approximately 2.5 mkA. This range depends on the given person's individual characteristics, as different patients (depending on their race, environment, situation, place of residence, etc.) have different normal BAPs electroskin resistance. When calculating a given patient's normal corridor, we try to foresee his or her individuality and use defining coefficients, such as those of Macumoto, Kabayashi, 1982. An individual normal corridor varies within a 15% range.

Figure 4:
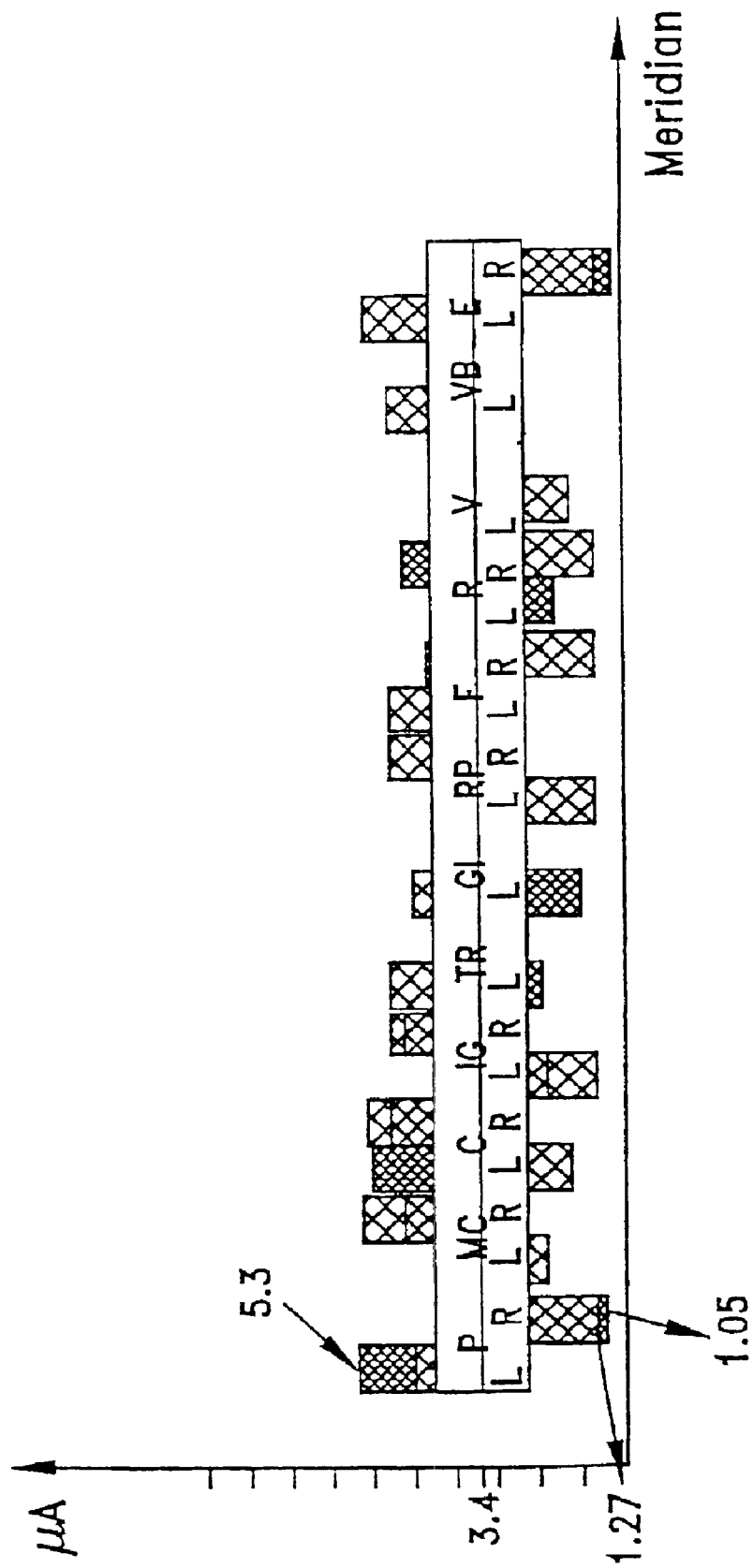
FIG. 4 schematically illustrates the process of the invention.

FIG. 4 schematically illustrates the process of the invention. The names of the 24 BAPs are written in parallel to the horizontal axis. The current measured at each point is marked on the ordinate. The normal corridor is shown as a horizontal stripe. The current readings falling within the corridor mean that there is no problem in the meridian (and its corresponding organ). If the figure appears above the normative corridor, the meridian is in an active state, its energy is too high. If the figure is below the corridor, the meridian's energy is too low.

In the classical Nakanty method (Japan, 1956) measurements are conducted in a similar way, but the difference is that one and the same average normative corridor is used for all the patients, and the 24 BAPs are measured only once, while in the case of this invention, it is possible to calculate and build the given patient's individualized normative corridor after the first series of tests, which is afterwards compared to the second normative corridor based on the data from measurements aftert electrostimulation. The results of the comparison are analyzed, and based on the information about the resulting deviations, a diagnosis can be made.

The above approach considerably decreases the percentage of mistakes in diagnostics. If the meridian is not within the normative corridor both before and after electrostimulation, there exists some organic disorder in the corresponding organ. If there are deviations in the meridian only before or after the stimulation, it means that there are only functional problems present in the corresponding organ. The algorithms of differentiated medical conclusions are based upon those typical of a given disorder association of meridian deviations, and not on a single meridian's deflections.

The resulting information can be either confirmed or questioned by conducting further testing of the announcement points and sympathetic points. They are measured straight after the completion of the first part of the test, first on the abdomen, and then on the back of the patient. Then the zero energy of announcement points and sympathetic points is measured, the results treated with the help of a special program, and a medical conclusion is reached. If the diagnosis coincides with that of the first part of the test, it is confirmed. If not—additional testing should be conducted (which is recommended by the program on the spot).

While embodiments of the invention have been described for purposes of illustration, it will be understood that the invention can be carried out with many modifications, variations and adaptations, without departing from its spirit or exceeding the scope of the claims.

What is claimed is:

1. Diagnostic method, comprising the steps of selecting 24 biologically active points (BAPs), measuring the skin resistance at said points, plotting the average resistance for said points as an isoelectric line and defining a normal corridor, further comprising the steps of:

A-a stimulation is applied to each of the said points,

B-the skin resistance is measured once again at said points after applying the stimulation, C-the results of the two sets of measurements are compared, and D-diagnostic conclusions are reached from their comparison.

2. Method according to claim 1, wherein the diagnostic conclusions comprise the following:

I-If a result obtained from the first set of measurements falls outside the normal corridor, this is considered a potential indicator of disease activity, II-if the corresponding result obtained from the second set of measurements (after stimulation) also lies outside the normal corridor, this is considered as a true indication of the presence of a disease, III-If, however, the corresponding result from the second set of measurements falls within the normal corridor, then the first measurement is considered not to be an indication of a true disease state and is therefore disregarded, and IV-If there are deviations in the meridian (outside the normal corridor) only after the stimulation, this is considered an indication of the presence of functional problems only in the corresponding organ.

3. Method according to claim 1, further comprising the steps of, if an indication of a disease state in a given organ or organ system is found:

a-measuring the electrical resistance of the relevant announcement point;

b-measuring the electrical resistance of the abdominal zero point;

c-calculating the ratio between the said two results; and d-drawing diagnostic conclusions from said calculated ratio.

4. Method according to claim 1, comprising the following steps:

I-measuring the electric resistance of the skin at the 24 BAPs in the feet and hands of the patient;

II-applying a stimulation to the BAPs by means of a skin electropunctural probe;

III-repeating the measurement of the electric resistance of the skin at the 24 BAPs;

IV-taking electric resistance measurements of the 10 announcement points on the abdomen;

V-measuring the parameters of the 12 sympathetic points in the paravertebral zone;

VI-measuring the zero energy for announcement points and for sympathetic points; and VII-mathematically processing the collected information.

5. Method according to claim 1, further comprising previously treating the BAPs with 70% ethyl alcohol solution.

6. Method according to claim 1, wherein the stimulation is carried out repeatedly on each BAP for one minute each time.

7. Method according to claim 1, further comprising the steps of adding together the 48 data received from 24 BAPs before and after the stimulation, dividing the results by 24, plotting the figures thus obtained as the ordinate on a diagram on which the BAPs are marked as the abscissa, connecting the points thus obtained to form the individual isoelectrical curve of the patient, and drawing two parallel lines above and below said isoelectrical curve to define the normative corridor of the patient.

8. Method according to claim 1, wherein the stimulation is carried out by stimulating GI4 on the left arm, GI4 on the right arm, E36 on the left leg (calf) and E36 on the right leg (calf), each for one minute.

9. Method according to claim 4, wherein the collected information is processed according to the following steps:

a) The value of the electrical skin resistance is calculated;

b) The readings from symmetrical points are compared;

c) The readings of corresponding announcement points and segmental points (correlated along the segmental chain) are compared;

d) The index of each announcement point is compared with that of the reference point;

e) The readings of each segmental point are compared to the index of a relatively permanent electroskin resistance point; and f) The numerical data obtained from all the foregoing operations, are analyzed and compared with each other and, based on the results obtained, an opinion on the condition of a given organ and the processes going on there is formed.

10. Method according to any of the preceding claim 1, wherein the stimulation is electrical.

11. Method according to any of the preceding claim 1, wherein the stimulation is mechanical.

* * * * *

UNITED STATES PATENT AND TRADEMARK OFFICE
CERTIFICATE OF CORRECTION

PATENT NO. : 6,934,581 B2
DATED : August 23, 2005
INVENTOR(S) : Kanevsky

It is certified that error appears in the above-identified patent and that said Letters Patent is hereby corrected as shown below:

<u>Title page,</u>
After Item [22], insert:
-- PCT Filed: January 29, 2001

PCT No.: PCT/IL01/00086

PCT Pub. No. WO 01/56461

PCT Pub. Date: August 9, 2001 --.
Insert Item:
-- [30] Foreign Application Priority Data

Feb. 3, 2000    (IL)    134381 --.

Signed and Sealed this

Twenty-first Day of February, 2006

JON W. DUDAS
*Director of the United States Patent and Trademark Office*